United States Patent
Zappelli et al.

[11] Patent Number: 5,993,768
[45] Date of Patent: Nov. 30, 1999

[54] MESOPOROUS CRYSTALLINE COMPOSITION WITH A HIGH SURFACE AREA OF A TETRAVALENT METAL WHICH CAN BE USED AS CATALYST

[75] Inventors: Piergiorgio Zappelli, Monterotondo; Giulio Alberti; Mario Casciola, both of Perugia; Fabio Marmottini, Deruta; Riccardo Vivani, Perugia, all of Italy

[73] Assignee: Eniricerche S.p.A., S. Donato Milanese, Italy

[21] Appl. No.: 08/999,263

[22] Filed: Dec. 29, 1997

[30] Foreign Application Priority Data

Jan. 16, 1997 [IT] Italy ................... MI97A0074

[51] Int. Cl.⁶ ............... C01B 25/26; C01B 25/42
[52] U.S. Cl. ............... 423/305; 423/308; 502/208
[58] Field of Search ................. 423/305, 308, 423/309, 311

[56] References Cited

U.S. PATENT DOCUMENTS

| | | |
|---|---|---|
| 4,180,551 | 12/1979 | Clearfield . |
| 4,609,484 | 9/1986 | Alberti et al. ............. 423/309 |
| 4,629,656 | 12/1986 | Alberti et al. ............. 423/309 |
| 4,721,738 | 1/1988 | Ellis et al. . |
| 5,166,380 | 11/1992 | Alberti et al. ............. 556/19 |
| 5,290,746 | 3/1994 | Alberti et al. . |

FOREIGN PATENT DOCUMENTS 0 736 539  10/1993  European Pat. Off. .
WO 92/18449  10/1992  WIPO .

*Primary Examiner*—Wayne Langel
*Attorney, Agent, or Firm*—Oblon, Spivak, McClelland, Maier & Neustadt, P.C.

[57] ABSTRACT

Solid mesoporous crystalline composition of a pyrophosphate-phosphate of a tetravalent metal, with a high surface area and narrow distribution of the mesopores, having formula (I):

$$M(P_2O_7)_{1-z}(HPO_4)_{2z} \qquad (I)$$

wherein: M is a tetravalent metal and z varies from 0.05 to 0.25.

The process for its production is described together with its uses.

4 Claims, 7 Drawing Sheets

MESOPOROUS CRYSTALLINE COMPOSITION WITH A HIGH SURFACE AREA OF A TETRAVALENT METAL WHICH CAN BE USED AS CATALYST

BACKGROUND OF THE INVENTION

1. Field of the Invention

The present invention relates to a solid mesoporous crystalline composition of a pyrophosphate-phosphate of a tetravalent metal, characterized by a high surface area and a narrow distribution of mesopores, the process for its production and its uses.

2. Description of the Background

G. Alberti, S. Allulli, U. Costantino and N. Tomassini, in J. Inorg. Nucl. Chem., 40, 1113 (1978), described the production of lamellar phosphonates of tetravalent metals, with a structure similar to that of zirconium alpha-phosphate [$\alpha$-Zr(HPO$_4$)$_2$.H$_2$O], by reactions between phosphonic acids and the salts of tetravalent metals. These lamellar phosphonates can be represented by the general formula M(RPO$_3$)$_2$, wherein M is a tetravalent metal and R an organic radical. A specific example is benzene zirconium phosphonate whose structure is shown in FIG. 1.

After this basic discovery, an intense research activity was carried out in this field, owing to the considerable applicative potentiality of the compounds obtained and in particular the following scientific patent literature can be mentioned: G. Alberti, U. Costantino and M. L. Luciani, J. Chromatog., 180, 45 (1979); G. Alberti and U. Costantino, J. Mol. Catal., 27, 235 (1984); G. Alberti, U. Costantino, J. Korney and M. L. Luciani, Reactive Polymers, 4, 1 (1985); G. Alberti, U. Costantino and G. Perego, J. Solid State Chem., 63, 455 (1986); EP 10.366; EP 10.857; M. B. Dines and P. M. Di Giacomo, Inorg. Chem. 20, 92 (1981); P. M. Di Giacomo and M. B. Dines, Polyhedron, 1, 61 (1982); M. B. Dines, P. M. Di Giacomo, K. P. Collahan, P. C. Griffith, R. H. Lane and R. E. Cooksey, A.C.S. Series 192, Chap.13, ACS, Washington DC, 1982; M. B. Dines, R. E. Cooksey, P. C. Griffith and R. H. Lane, Inorg. Chem. 22, 1003 (1983); M. B. Dines and P. C. Griffith, Polyhedron 2, 607 (1983); C. Y. Ortiz-Avila and A. Clearfield, Inorg. Chem. 24, 1773 (1985); A. Clearfield, Design of New Materials, Plenum Press, New York (1987), pages 121–134; and A. Clearfield, Chem. Rev. 88, 125 (1988).

EP 10.366 and EP 10.857 describe some compositions of the column or "pillared" type, obtained by reactions between salts of tetravalent metals and diphosphonic acids, with the formula M$^{IV}$[R(PO$_3$)$_2$], (wherein M is a tetravalent metal and R is a bivalent organic radical), whose structure is schematically illustrated in FIG. 2. In order to obtain compounds which can be used as molecular sieves, an attempt was made to introduce a certain degree of microporosity between the layers; a proposal was then made to dilute the columns in the interlayer zone, by partially substituting them with very small groups of the type R'PO$_3$, such as for example phosphite, HPO$_3$ groups. EP 492/694 describes the preparation of a diphosphonate-phosphite of a tetravalent metal having a high degree of crystallinity and a high degree of porosity which can be attributed to microcavities in the interlayer region induced by the presence of regularly distributed phosphite groups.

U.S. Pat. No. 5,166,380, as well as Italian Patent applications 95/A000710 and 96A/001106, subsequently disclosed that it is possible to prepare a diphosphonate-phosphite of a tetravalent metal, in crystalline form, under such conditions that the HPO$_3$ groups, in addition to the formation or non-formation of micropores in the interlayer region, also induce the formation of mesoporosity, which cannot be attributed to the formation of cavities in the interlayer region, characterized by a rather narrow distribution of the pore dimensions, most of which have dimensions within the range of 20–30 Å.

SUMMARY OF THE INVENTION

We have now surprisingly found that it is possible to obtain a mesoporous compound with a high surface area, completely inorganic, by the calcination of a composition of diphosphate phosphite of a tetravalent metal.

In accordance with this, the present invention relates to an inorganic composition which can be defined as a pyrophosphate-phosphate having the formula:

$$M(P_2O_7)_{1-z}(HPO_4)_{2z} \qquad (I)$$

wherein M is a tetravalent metal, selected from zirconium, titanium and tin, and z can vary from 0.05 to 0.25, said compound being in the form of a crystalline solid having the following characteristics:
  lamellar structure, completely inorganic, $\alpha$-type,
  B.E.T. surface area from 100 to 250 m$^2$/g,
  porosity within the range of mesopores, with at least 90% of the pores with a diameter greater than or equal to 30 Å and less than or equal to 50 Å,
  thermal stability up to 700° C.,
  ion conductivity, measured at 20° C. and at 75% of relative humidity, between 1.10$^{-4}$ and 6.10$^{-4}$ S cm$^{-1}$.

A further object of the present invention relates to the process for the preparation of the compound having formula I described above, comprising:
  calcination in air for 10–24 hours at 500–700° C. of a phosphate composition of a tetravalent metal having the general formula:

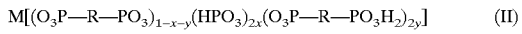

$$M[(O_3P{-}R{-}PO_3)_{1-x-y}(HPO_3)_{2x}(O_3P{-}R{-}PO_3H_2)_{2y}] \qquad (II)$$

wherein: M is a tetravalent metal, R is a bivalent organic radical, x varies from 0.3 to 0.6, y varies from 0.05 to 0.3,
  said composition having a lamellar, $\alpha$-type structure with an interlayer distance of 7.4 to 20 Å, a B.E.T. surface area ranging from 250 to 400 m$^2$/g, a porosity within the range of mesopores, with at least 50% of the pores with a diameter greater than or equal to 30 Å and less than or equal to 50 Å,
  said composition having formula (II) being obtained by reacting a diphosphonic acid R(PO$_3$H$_2$)$_2$, phosphorous acid H$_3$PO$_3$, an oxychloride of a tetravalent metal MOCl$_2$, in a solvent selected from: n-propanol, water or dimethylsulfoxide, wherein M and R having the meaning defined above.

Figure 1:
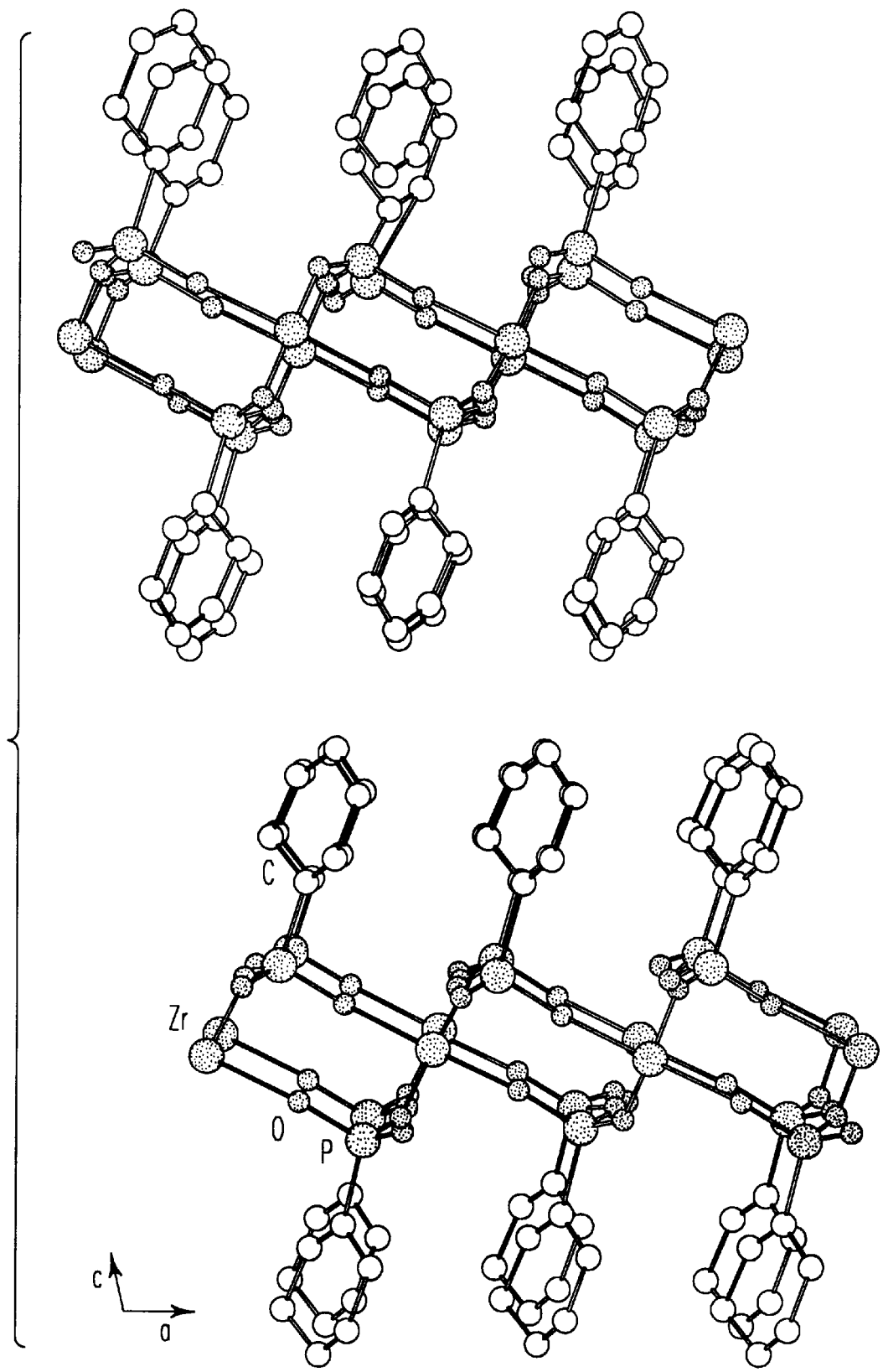
FIG. 1 shows the molecular structure of benzene zirconium phosphonate.
Figure 2:
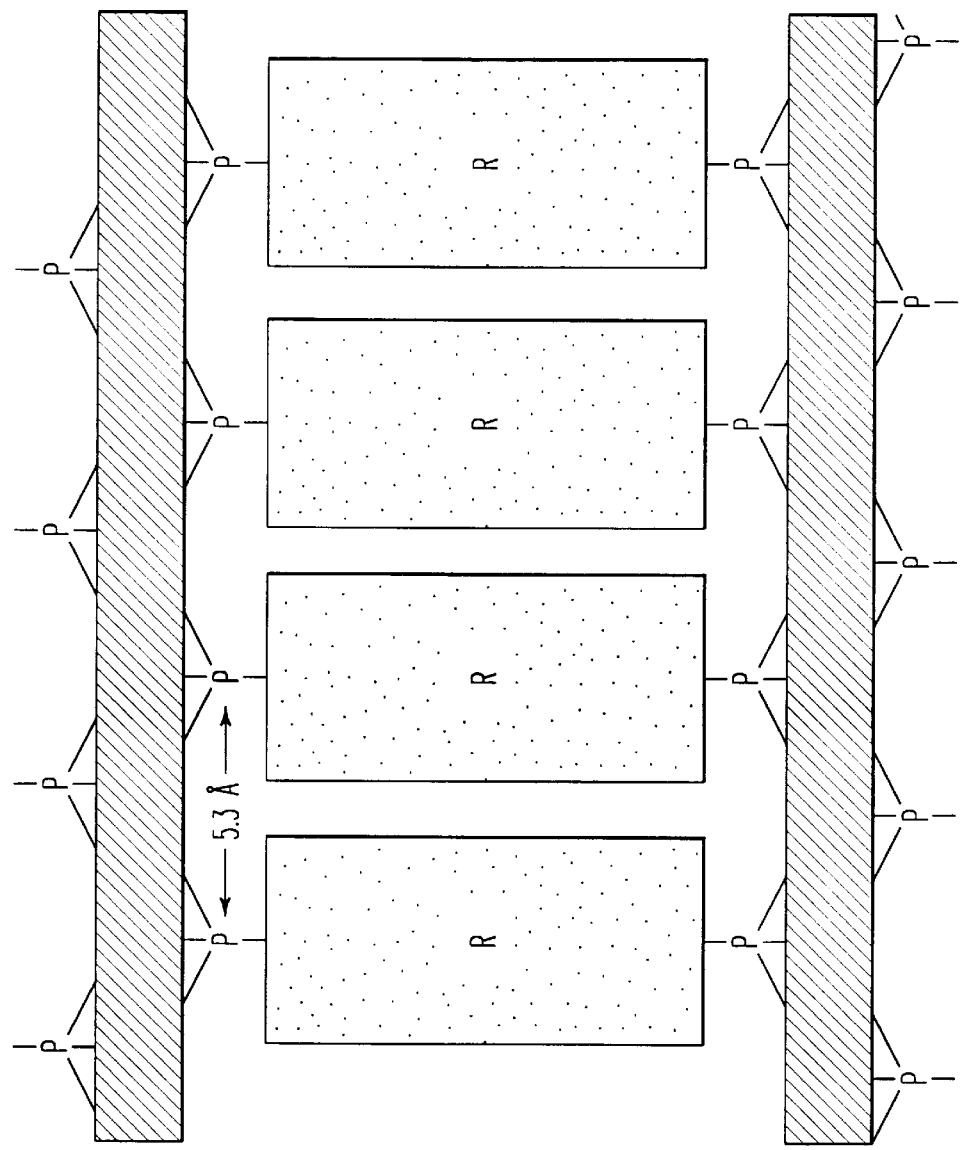
FIG. 2 is a schematic illustration of the pillared product obtained by reacting salts of tetravalent metals and diphosphonic acid.

The process for the preparation of the composition having formula II is already described in Italian patent application 95/00710. The subsequent transformation, by means of a calcination process in air, into the composition having formula (I), takes place according to the following reaction:

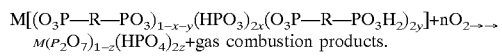
$$M[(O_3P-R-PO_3)_{1-x-y}(HPO_3)_{2x}(O_3P-R-PO_3H_2)_{2y}]+nO_2 \rightarrow$$
$$M(P_2O_7)_{1-z}(HPO_4)_{2z}+\text{gas combustion products.}$$

The calcination is carried out for a time ranging from 10 to 24 hours at a temperature ranging from 500 to 700° C.

The non-complete transformation of the composition having formula (II) into $MP_2O_7$ can be understood by considering the behaviour of the calcination of α-type microcrystalline zirconium phosphate. It is known, in fact, that at temperatures between 300 and 600° C., all the $HPO_4$ groups present in the interlamellar regions condense to pyrophosphate groups. This condensation is not possible however for the $HPO_4$ groups which are located on the surface of the microcrystals. The condensation of these latter groups can only take place at temperatures higher than 800–900° C., i.e. when the lamellar structure undergoes an overall re-arrangement to pass to a tridimensional structure of the cubic type (G. Alberti, M. Casciola, U. Costantino and M. Leonardi, Solid State Ionics, 14, 289 (1984).

Consequently, having calcined the product at 600° C., the residual $HPO_4$ groups in the composition having formula (I) can be attributed to surface groups. The presence of surface $HPO_4$ acid groups is also confirmed by the high protonic conductivity of the material in question. It is known in fact that in α-type microcrystalline acid zirconium phosphate, the electric conductivity, measured with the impedance method ("Impedance Spectroscopy", J. R. Macdonald ed., John Wiley & Sons, 1987, chap. 4), is proportional to the surface area, i.e. to the number of $O_3POH$ groups present on the surface of the microcrystals (G. Alberti, M. Casciola, U. Costantino, G. Levi and G. Ricciardi, J. Inorg. Nucl. Chem. 40, 533 (1978)).

The material of the present application, represents significant progress, with respect to the known art, in the production of materials based on zirconium phosphate with a high surface area. α-type, microcrystalline zirconium phosphate is in fact characterized by a very small surface area (0.5–1 m²/g) and various attempts at increasing its surface development to over 20 m²/g have proved negative. Approaches comprising the use of organic pillars under particular conditions, as described in U.S. Pat. No. 5,166,380 and in Italian patent applications 95A/000710 and 96A/001106, have produced materials with a high surface area and with a porosity having a narrow distribution within the range of mesopores. The latter materials however, having an organic component inside, had the same limits of thermal stability as these organic components. The great innovation of the present invention consists in the production of a material substantially having the surface area and porosity properties obtained with the organic-inorganic materials previously mentioned, but with the thermal stability of a totally inorganic material. Owing to the narrow distribution of the mesopores in the region of 30–50 Å, the solid crystalline compositions of the present invention are of great interest as molecular sieves for large molecules. In addition, due to its characteristics of acidity, high surface area and thermal stability (>600° C.), the catalyst can be used in reactions for which an acid catalysis is required at a high temperature, in particular in the conversions of hydrocarbons, such as for example alkylation, etherification, isomerization, dehydrogenation reactions. The following examples provide a better illustration of the present invention but do not limit its scope.

EXAMPLE 1

Preparation of the mesoporous precursor zirconium phenylenediphosphonate-phosphite (II)

The composition was prepared according to what is described in Italian Patent Application 95A/000710, as follows:

7.14 g of 1,4-phenylenediphosphonic acid and 11.48 g of phosphorous acid (Carlo Erba RPE reagent) are dissolved in 700 ml of n-propanol (Carlo Erba RPE), contained in a plastic container. 16.11 g of $ZrOCl_2.8H_2O$ (Merck, proanalysis) dissolved in 34.5 ml of concentrated HF (50% by weight, Carlo Erba RPE) and 65.5 ml of n-propanol are added to the clear solution, maintained at 80° C. The solution thus obtained has the following composition: $[C_6H_4(PO_3H_2)_2]=0.038$ M, $[H_3PO_3]=0.175$ M, $[Zr^{IV}]=0.063$ M, $[HF]=1.25$ M. The solution is maintained at 80° C. for 8 hours, care being taken that the volume remains constant. After this period the microcrystalline solid formed is separated from the solution by centrifugation, washed three times with about 500 ml of n-propanol and finally dried in an oven at 60° C. The solid zirconium diphosphonate-phosphite thus obtained is conserved in a vacuum drier containing phosphoric anhydride.

The product thus obtained is characterized with the following procedures. To discover the molar ratio diphosphonic acid/phosphorous acid in the solid, the nuclear magnetic resonance technique of $^{31}P$ is used. About 20 mg of solid are dissolved in a few drops of concentrated hydrofluoric acid, 1 ml of dimethylsulfoxide deuterate (DMSO-$D_6$, Carlo Erba RPE) is added, and the product is analyzed with a Bruker AC200 spectrometer. The molar ratio proves to be equal to 0.84:1.

Figure 3:
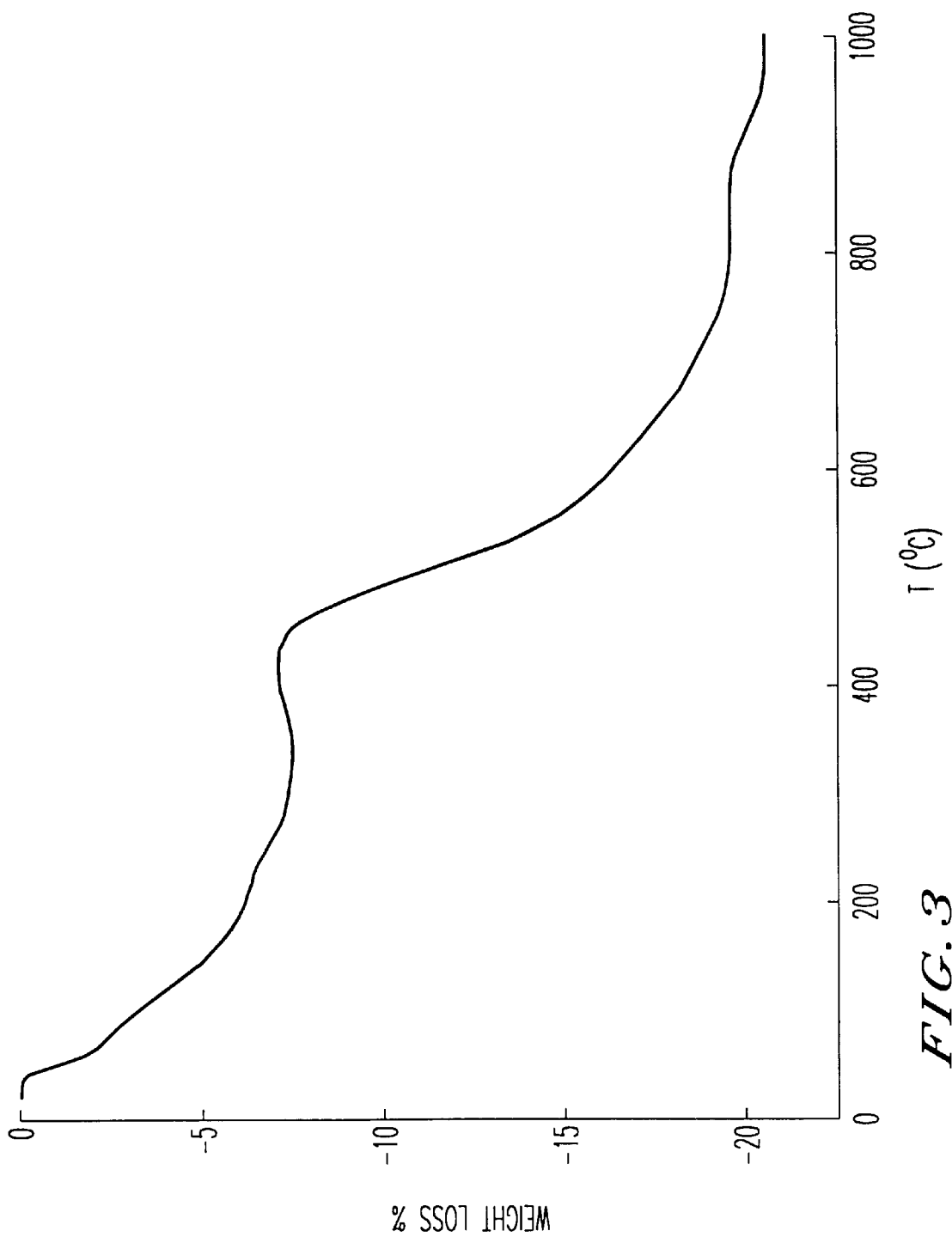
FIG. 3 is a weight loss curve, obtained by thermogravimetric analysis, of solid zirconium diphosphonate-phosphite.

To determine the composition of the solid a thermogravimetric analysis was carried out. The weight loss curve, illustrated in FIG. 3, shows a loss of 7.43% within the range of 20–250° C., due to solvent adsorbed in the sample, then a second weight loss equal to 12.14%, within the range of 250–800° C. due to oxidation of the organic part, oxidation of the phosphite groups to phosphate groups and condensation of the latter to pyrophosphate groups. A third small weight loss, equal to 1.0% within the range of 800–1000° C. is due to the condensation of the phosphate groups on the surface of the microcrystals and formation of zirconium pyrophosphate with a cubic structure, having the formula $ZrP_2O_7$. From the NMR and thermogravimetry data, it is possible to determine the following composition:

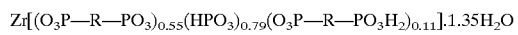
$$Zr[(O_3P-R-PO_3)_{0.55}(HPO_3)_{0.79}(O_3P-R-PO_3H_2)_{0.11}].1.35H_2O$$

Figure 4:
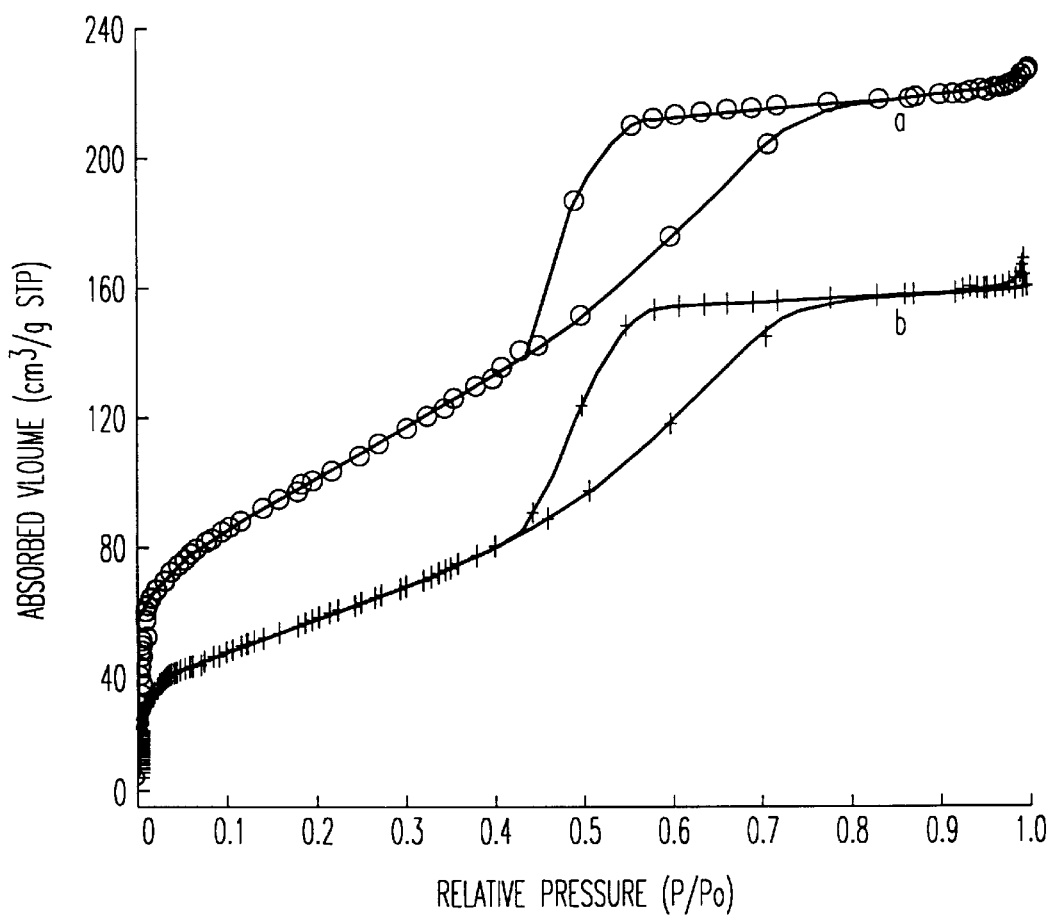
FIG. 4 is an adsorption-desorption isotherm showing a hysteresis loop characteristic of mesoporous solids.
Figure 5:
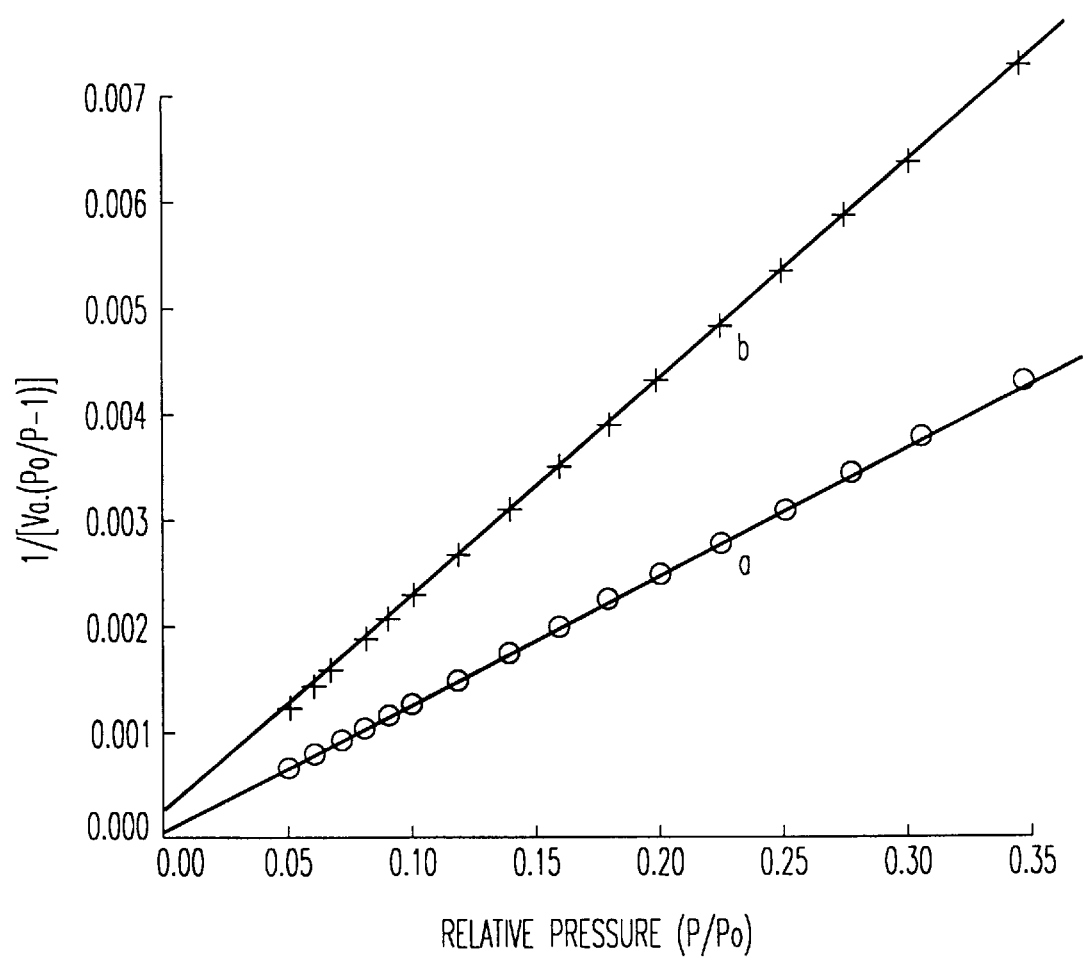
FIG. 5 is a mathematical treatment of the isotherm of FIG. 4 according to BET theory.

To obtain the porosity characteristics, the solid is first degassed at a temperature of 250° C. and at a pressure of $10^5$ torr for 12 hours. A measurement of the surface area is then carried out by adsorption of nitrogen using a Micromeritics ASAP 2010 instrument. The adsorption and desorption isotherm, shown in FIG. 4 (curve a) shows a hysteresis loop which is typical of mesoporous solids. The mathematical treatment of the isotherm according to the B.E.T. theory, of which a plot is shown in FIG. 5 (line a), gives a specific surface area of 357 m$^2$/g. The nitrogen adsorption and desorption data are treated according to the t-plot method (B. C. Lippens and J. H. de Boer, J. Catalysis, 4, 319 (1965)) to obtain the volume of the micropores (within the porosity range of 5–20 Å in diameter) and according to the B.J.H. method (E. P. Barrett, L. G. Joyner and P. H. Halenda, J. Am.Chem. Soc., 73, 373 (1951)) to obtain the volume of the mesopores (within the porosity range of 20–200 Å in diameter). A micropore volume of 0.029 cm$^3$/g and a mesopore volume of 0.294 cm$^3$/g was thus estimated. The diameter of the micropores, obtained by application of the MP method (R. Sh. Mikhail, S. Brunauer and E. E. Bodor, J. Colloid Interface Sci., 26, 45, (1968), 54), is very small (4–5 Å), close to the sensitivity limit of the method.

Figure 6:
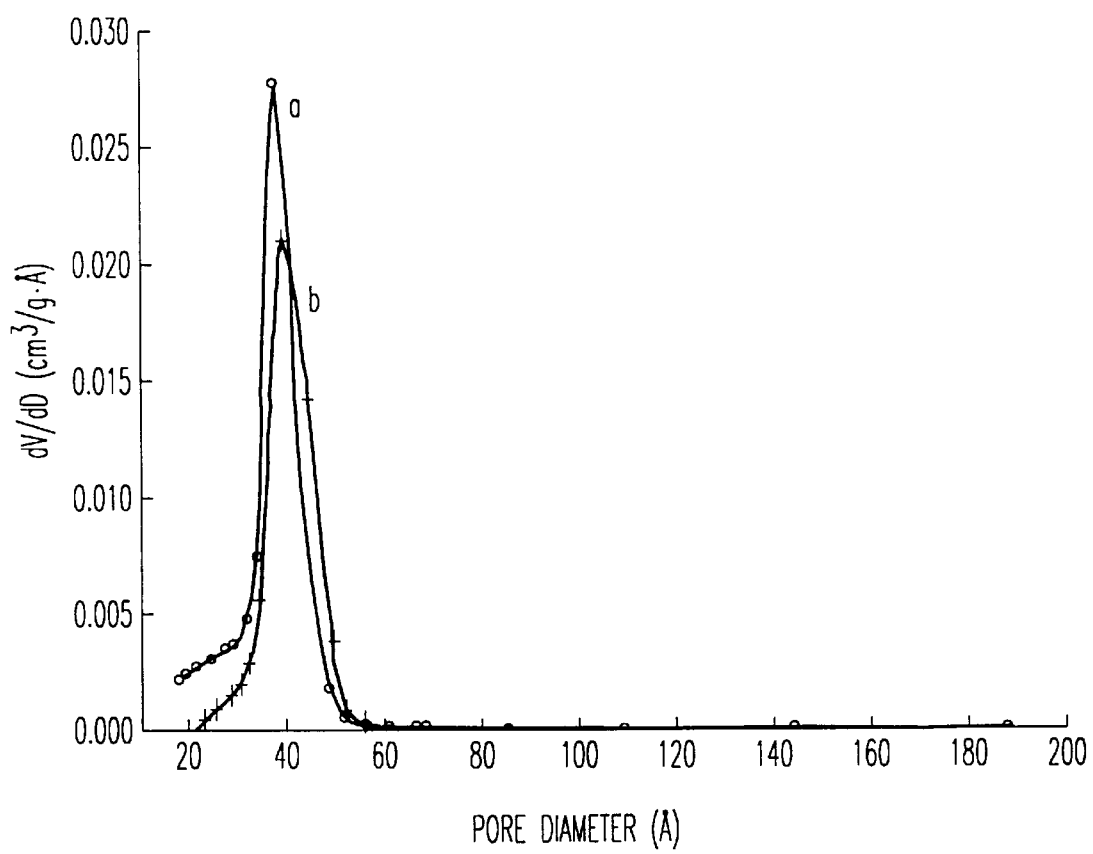
FIG. 6 shows the differential distribution curve of pores of the zirconium pyrophosphate material of Example 1.
Figure 7:
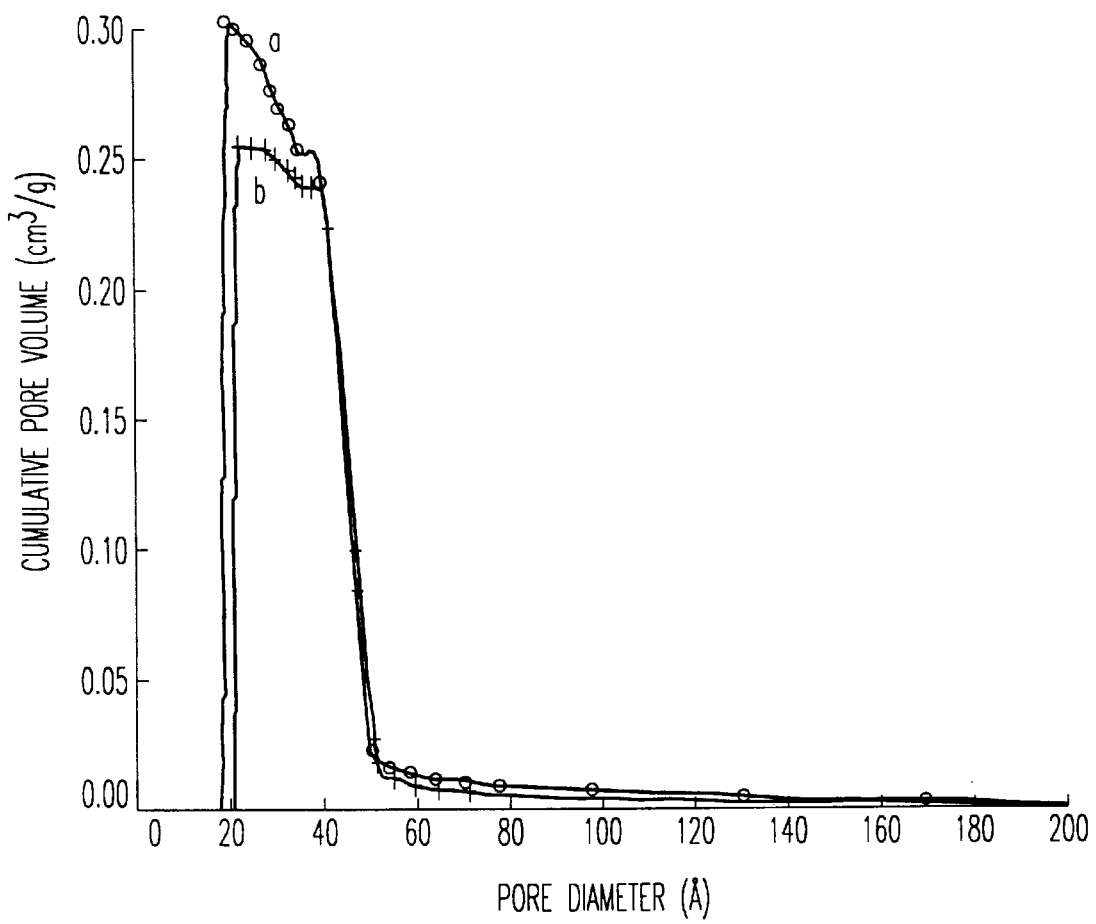
FIG. 7 shows the total volume of pores of the zirconium pyrophosphate product of Example 1.

FIG. 6 (curve a) shows the differential distribution curve of the pores calculated by means of the desorption data, whereas FIG. 7 (curve a) shows the total volume of the pores in relation to their dimension, or cumulative distribution curve of the pores. The differential distribution curve of the pores shows a single strong maximum corresponding to pores with a diameter of 37 Å, which represents the most probable value. From these curves it is calculated that 90% of the mesopore volume is between 30 and 50 Å in diameter.

EXAMPLE 2

Preparation of mesoporous crystalline zirconium pyrophosphate-phosphate (I)

The composition

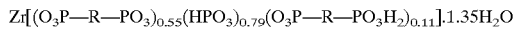
$Zr[(O_3P—R—PO_3)_{0.55}(HPO_3)_{0.79}(O_3P—R—PO_3H_2)_{0.11}] \cdot 1.35H_2O$ (formula weight=333.6), obtained as in Example 1, is subjected to calcination in air. The calcination is carried out for 16 hours at 600° C. During this calcination the precursor loses 19.57% of its initial weight. From this value a formula weight of the composition in question is calculated equal to 268.3, and then a value of z in formula (I) equal to 0.17. The product obtained therefore has the composition:

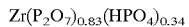
$Zr(P_2O_7)_{0.83}(HPO_4)_{0.34}$

It is then possible to write the following decomposition reaction which takes place during the calcination process:

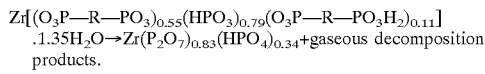
$Zr[(O_3P—R—PO_3)_{0.55}(HPO_3)_{0.79}(O_3P—R—PO_3H_2)_{0.11}]$
$\cdot 1.35H_2O \rightarrow Zr(P_2O_7)_{0.83}(HPO_4)_{0.34}$+gaseous decomposition products.

To confirm the composition of the material obtained, it was heated to 1000° C. immediately after its preparation. At this temperature, as previously specified, there is a transition of the lamellar α-type structure to a tridimensional cubic lattice structure. In this phase transition the surface HPO$_4$ groups condense to pyrophosphate groups according to the reaction:

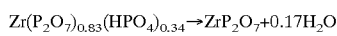
$Zr(P_2O_7)_{0.83}(HPO_4)_{0.34} \rightarrow ZrP_2O_7 + 0.17H_2O$

The loss in experimental weight for this transformation is equal to 1.5% of the initial weight, in accordance with the calculated value (1.2%).

The product obtained from the calcination process at 600° C. was analyzed by nitrogen adsorption according to what is described in Example 1, with the only difference that the degassing temperature used in this case is 350° C. The specific surface area proved to be equal to 215 m$^2$/g, with a micropore volume of 0.009 cm$^3$/g and a mesopore volume equal to 0.260 cm$^3$/g. FIGS. 4 and 5 (curve b) respectively show the adsorption and desorption isotherm and the B.E.T. plot for the product in question. The differential distribution curve of the pores (FIG. 6, curve b) shows a single strong maximum corresponding to pores with a diameter of 38 Å, which represents the most probable value. FIG. 7 (curve b) shows the total volume of the pores in relation to their dimension, or cumulative distribution curve of the pores for the product in question. From these curves it is calculated that 90% of the mesopore volume is between 30 and 50 Å in diameter. The volume of the micropores in this case is negligible. From a comparison with the data previously indicated for the precursor (example 1), it can be seen that about 89% of the mesopore volume was conserved after calcination under the conditions described, whereas the pore dimensions remained practically unchanged.

The measurement of the surface area provides an alternative method for determining the composition of the material. Since, as in zirconium phosphates and phosphonates with an α-type structure, an area of about 24 Å$^2$ can be reasonably assigned to each phosphate group, the value of z in formula (I) can be calculated by means of the following equation:

$$z=(S \cdot M \cdot 10^{20})/(2 \cdot 24 \cdot 6.023 \cdot 10^{23})$$

wherein S is the specific surface area value in m$^2$/g of composition and M is the formula weight of the composition. Applying this equation, a value of z equal to 0.19 can be calculated, from which it is possible to obtain the following composition:

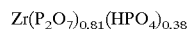
$Zr(P_2O_7)_{0.81}(HPO_4)_{0.38}$ which is in accordance with what was obtained by gravimetric analysis. This accordance also shows the nature of the surface sites.

The composition of the material in question was also confirmed by protonic conductivity measurements, in particular by a comparison between the protonic conductivity of the material in question with that of a sample of microcrystalline zirconium phosphate. These conductivity measurements were carried out on tablets, by pressing, at 40 kN/cm$^2$, about 200 mg of the samples in question. The two sides of the tablets were covered with gold electrodes deposited by sputtering and the tablets were subsequently equilibrated, at room temperature, 75% of relative humidity. The protonic conductivity was measured at 20° C. and 75% of relative humidity by the impedance technique, within the frequency range of 10 Hz–10 MHz. It was found that the conductivity of the composition in question, which has a surface area equal to 215 m$^2$/g, is equal to $4.5 \cdot 10^{-4}$ S cm$^{-1}$, whereas that of zirconium α-phosphate, having a surface area equal to 1 m$^2$/g, is $2.0 \cdot 10^{-6}$ cm$^{-1}$. The ratio between the ionic conductivity values is 225, and therefore practically equal to the ratio between the relative surface areas. Since, as already specified, in microcrystalline zirconium phosphate with α structure, the protonic conductivity value is proportional to the number of HPO$_4$ groups present on the surface of the microcrystals, this result indicates that the material in question has a high surface area characterized by acid groups similar to those present on the surface of α-type microcrystalline zirconium phosphate.

The surface area observed on the materials obtained with the process of the present application, although slightly reduced with respect to that of the starting organic-inorganic composition, forms the highest value found so far for an α-type zirconium phosphate.

We claim:

1. A pyrophosphate-phosphate compound having the formula:

$$M(P_2O_7)_{1-z}(HPO_4)_{2z} \quad (I)$$

wherein: M is a tetravalent metal selected from the group consisting of zirconium, titanium and tin, and z varies from 0.05 to 0.25, said compound being in the form of a crystalline solid and having the following characteristics:
lamellar structure, completely inorganic, α-type,
B.E.T. surface area from 100 to 250 m$^2$/g,
porosity within the range of mesopores, with at least 90% of the pores with a diameter greater than or equal to 30 Å and less than or equal to 50 Å,
thermal stability up to 700° C.,
ion conductivity, measured at 20° C. and at 75% of relative humidity, between $1.10^{-4}$ and $6.10^{-4}$ S cm$^{-1}$.

2. The compound according to claim 1, wherein the metal is zirconium.

3. A process for obtaining the compound of claim 1, comprising:
calcining, in air for 10–24 hours at 500–700° C., a phosphate composition of a tetravalent metal having the formula:

$$M[(O_3P-R-PO_3)_{1-x-y}(HPO_3)_{2x}(O_3P-R-PO_3H_2)_{2y}] \quad (II)$$

wherein:

M is a tetravalent metal selected from the group consisting of zirconium, titanium and tin, R is a bivalent organic radical, x varies from 0.3–0.6, y varies from 0.05–0.3, said composition having a lamellar, α-type structure with an interlayer distance of 7.4–20 Å, a B.E.T. surface area ranging from 250–400 m$^2$/g, a porosity within the range of mesopores, with at least 50% of the pores with a diameter greater than or equal to 30 Å and less than or equal to 50 Å, said composition having formula (II) being obtained by reacting a diphosphonic acid $R(PO_3H_2)_2$, phosphorous acid $H_3PO_3$, an oxychloride of a tetravalent metal $MOCl_2$, in a solvent selected from the group consisting of: n-propanol, water and dimethylsulfoxide, wherein M and R are as defined above.

4. The process of claim 3, wherein said tetravalent metal is zirconium.

* * * * *